US00PP29448P2

(12) United States Plant Patent
Dirr

(10) Patent No.: US PP29,448 P2
(45) Date of Patent: Jul. 3, 2018

(54) ***GARDENIA* PLANT NAMED 'PIIGA-III'**

(50) Latin Name: *Gardenia jasminoides*
Varietal Denomination: PIIGA-III

(71) Applicant: Michael A. Dirr, Bogart, GA (US)

(72) Inventor: Michael A. Dirr, Bogart, GA (US)

(73) Assignee: BAILEY NURSERIES, INC., Newport, MN (US)

( * ) Notice: Subject to any disclaimer, the term of this patent is extended or adjusted under 35 U.S.C. 154(b) by 0 days.

(21) Appl. No.: 15/530,409

(22) Filed: Jan. 10, 2017

(51) Int. Cl.
*A01H 5/00* (2018.01)
*A01H 5/02* (2018.01)

(52) U.S. Cl.
USPC ..... Plt./255
CPC ..... *A01H 5/02* (2013.01)

(58) Field of Classification Search
USPC ..... Plt./255
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of *Gardenia* named 'PIIGA-III' that is characterized by its flowers that are medium in size, single, white in color and produced from spring to frost in Georgia, its foliage that is lustrous in appearance and dark green in color, its compact and mounding plant habit, and its cold hardiness at least to U.S.D.A. Zone 6b.

2 Drawing Sheets

Botanical classification: *Gardenia jasminoides*.
Variety denomination: 'PIIGA-III'.

BACKGROUND OF THE INVENTION

The present invention relates to a new and distinct cultivar of *Gardenia jasminoides*. The new cultivar will be referred to hereafter by its cultivar name, 'PIIGA-III'. 'PIIGA-III' is a new cultivar of *Gardenia* grown for use as a landscape shrub.

The new cultivar arose as a seedling in Watkinsville, Ga. from seeds planted from open pollination of unnamed and unpatented plants of *Gardenia jasminoides*. The Inventor selected the new cultivar as a single unique plant in 2009. The exact parentage is therefore unknown.

Asexual propagation of the new cultivar was first accomplished by semi-hardwood stem cuttings under the direction of the Inventor in Watkinsville, Ga. in 2009. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PIIGA-III' as a new and unique cultivar of *Gardenia*.

1. 'PIIGA-III' exhibits flowers that are medium in size, single, white in color and produced from spring to frost in Georgia.
2. 'PIIGA-III' exhibits foliage that is lustrous in appearance and dark green in color.
3. 'PIIGA-III' exhibits a compact and mounding plant habit.
4. 'PIIGA-III' exhibits a cold hardiness at least to U.S.D.A. Zone 6b.

'PIIGA-III' can be most closely compared to the *Gardenia jasminoides* cultivars 'Double Mint' (U.S. Plant Pat. No. 23,507) and 'Chuck Hayes' (U.S. Plant Pat. No. 28,755) and *Gardenia augusta* 'PIIGA-I' (U.S. Plant Pat. No. 22,510). All three are similar to 'PIIGA-III' in having flowers that are white in color and 'PIIGA-I' is also similar in having single flowers. 'Double Mint' differs from 'PIIGA-III' in having double flowers with more abundant re-bloom in fall and cold hardiness to U.S.D.A. Zone 7. 'Chuck Hayes' differs from 'PIIGA-III' in having double flowers, a larger growth habit, and foliage that is larger in size and often turns yellow-green in color in winter. 'PIIGA-I' differs from 'PIIGA-III' in having flowers that are larger in size, a more vigorous and larger plant habit, and in producing less fruit.

BRIEF DESCRIPTION OF THE DRAWINGS

The accompanying colored photographs illustrate the overall appearance and distinct characteristics of the new *Gardenia*. The photographs were taken of 8 year-old plants of the new cultivar as grown outdoors in the ground in Watkinsville, Ga.

The photograph in FIG. 1 provides a top view of 'PIIGA-III' in bloom.

Figure 1:
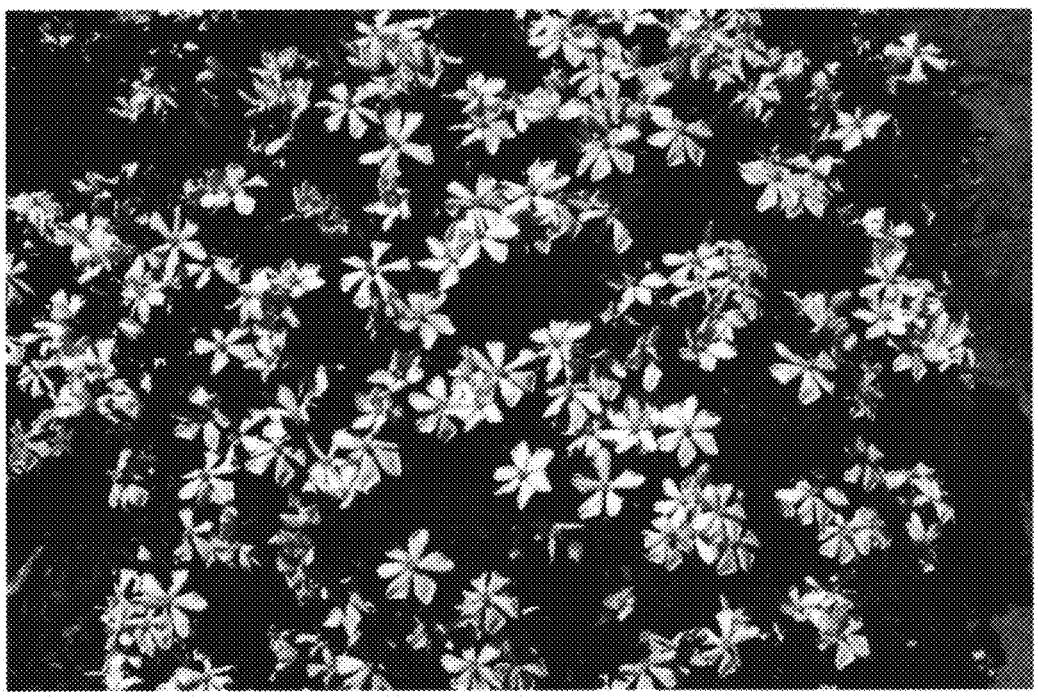
Figure 2:
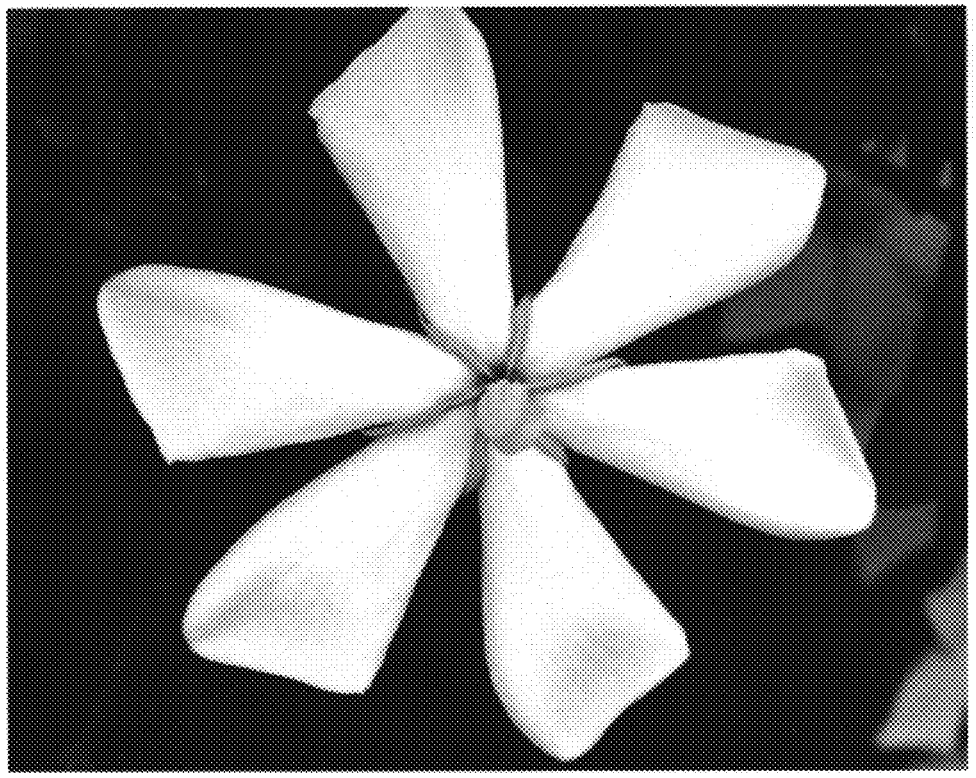

The photograph in FIG. 2 provides a close-up view of a flower of 'PIIGA-III'.

The colors in the photographs are as close as possible with the photographic and printing technology utilized and the color values cited in the detailed botanical description accurately describe the colors of the new *Gardenia*.

DETAILED BOTANICAL DESCRIPTION

The following is a detailed description of 10 year-old plants of the new cultivar as grown outdoors in the ground in Watkinsville, Ga. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming habit*.—Heavy blooming from May until June, then less blooming from June to October.

*Plant type*.—Evergreen shrub.

*Plant habit*.—Compact, mounded, freely branching.

*Height and spread*.—An average of 79 cm in height and 127 cm in width as an 8 year-old plant in the landscape.

*Cold hardiness*.—At least to U.S.D.A. Zone 6b.

*Diseases and pests*.—No susceptibility and resistance to diseases or pests has been observed.

*Propagation*.—Semi-hardwood stem cuttings.

*Growth rate*.—Moderately vigorous.

*Root description*.—Fibrous roots, 161A in color.

*Root development*.—About 6 weeks at 32° C. to initiate roots and about 4 months at 32° C. to produce a rooted young plant in summer.

Branch description:

*Branch color*.—Young growth; 144A, maturing growth and bark; 197A.

*Branch surface*.—Young; fine pubescence, young stems maturing; glabrous and becoming exfoliating, trunk; exfoliating bark.

*Branch shape*.—Round.

*Internode length*.—Average of 3 cm.

*Branch size*.—First year stems; an average of 20 cm in length and 3 mm in diameter, second year stems; an average of 43 cm in length and 5 mm in diameter, trunk; about 20 cm at soil line.

*Branch strength*.—Flexible when young, easily broken when mature.

*Stipules*.—None observed.

Foliage description:

*Leaf type*.—Simple.

*Leaf shape*.—Lanceolate.

*Leaf apex*.—Acuminate.

*Leaf base*.—Cuneate.

*Leaf size*.—Average of 4.5 cm in length, 1.5 cm in width.

*Leaf arrangement*.—Opposite, sometimes whorled.

*Leaf margin*.—Entire.

*Leaf venation*.—Pinnate, upper and lower surface 145A in color.

*Leaf color*.—Young upper surface; 141A, young lower surface; 139C, mature upper surface; N137A, mature lower surface; 146B.

*Leaf number*.—An average of 20 per branch 25 cm in length.

*Leaf surface*.—Upper and lower surface glabrous and lustrous.

*Leaf substance*.—Thick.

*Vegetative buds*.—Opposite arrangement, conical in shape, single-scaled, 3 mm in length and 1 mm in width, 144B in color.

*Petioles*.—An average of 2 mm in length and 3 mm in diameter, color 146B, surface glabrous.

Inflorescence description:

*Inflorescence type*.—Solitary from upper leaf axils.

*Flower number*.—An average of 2 to 3 per branch.

*Flower fragrance*.—Strong, pleasant fragrance typical of *Gardenia*.

*Flower longevity*.—Showy for an average of 3 days and remaining on plant for 1 to 2 weeks after they have senesced.

*Flower type*.—Salviform with lobes rotate.

*Flower size*.—An average of 5 cm in diameter and 3 cm in depth.

*Flower buds*.—Oblong in shape, an average of 0.5 mm in diameter and 2.5 cm in length, glabrous surface, 144B in color.

*Corolla lobes*.—An average of 6 per flower, arranged in a single whorl, none overlapping at base, primarily obovate in shape, average of 2.5 cm in length, 7.5 mm in width, rounded to truncate apex, margins entire, base cuneate and fused into the corolla tube, aspect is primarily horizontal and slightly wavy, color when young opening and fully open NN155B and maturing to 11C and fading to N199D.

*Corolla tube*.—An average of 2.5 cm in length and 5 mm in width, surface texture; outer surface glabrous and inner surface is pubescent, color of inside surface is 150C and color of outside surface is 144B.

*Calyx*.—An average of 2.5 cm in length and 1.5 cm in diameter, 143A inner surface, 142A lower surface, star shaped.

*Sepals*.—5, 60%, fused at base, an average of 2.5 cm, 5 mm in width, lanceolate in shape, acute apex, entire margin, upper and lower surface color is 144B, upper and lower surface is smooth and glabrous.

*Peduncles*.—Round in shape, held upright, strong strength, average of 6 mm in length and 3 mm in diameter, glossy and smooth surface, 143A in color.

*Pedicels*.—Round in shape, average of 2 cm in length, 7 mm in diameter, glabrous surface and 143A in color.

Reproductive organs:

*Gynoecium*.—1 pistil, 1.8 cm in length, 4 mm in diameter, inferior, stigma; obovate in shape, 7 mm in length, 4 mm in width, 154C in color, style; 2.5 cm in length and 1.5 mm in width, tubular in shape, 154D in color, ovary; 5 mm in length and 4 mm in width, elliptoid in shape, 160D in color, containing an average of 50, minute shiny ovules less than 1 mm in diameter.

*Androecium*.—An average of 6 stamens, filaments; no distinguishable, anthers; fused to petal lobes, an average of 8 mm in length and 2 mm in width, lanceolate in shape, 199B in color, pollen is low in quantity and 9A in color.

*Fruit and seed*.—Berry, six-winged, oval in shape, average of 2.5 cm in length and 2 cm in diameter, N163C in color at maturity, abundant in quantity (about 150 on a 2 year-old plant) with quantity dependent on size and maturity of plant, seed; numerous (at least 100 per berry), round in shape, 2.5 mm in diameter, 164C in color.

It is claimed:

1. A new and distinct cultivar of *Gardenia* plant named 'PIIGA-III' as herein illustrated and described.

* * * * *